United States Patent
Sanchez et al.

(10) Patent No.: US 10,779,525 B2
(45) Date of Patent: Sep. 22, 2020

(54) TREATMENT COMPOUND AND METHOD OF APPLICATION FOR HOOF OR FOOT DISEASE IN ANIMALS

(71) Applicant: Zin Research LLC, Lancaster, MO (US)

(72) Inventors: John P. Sanchez, Mesa, AZ (US); Diane Sanchez, Lancaster, MO (US); Michael Sanchez, Woodbury, MN (US)

(73) Assignee: Zin Research LLC, Lancaster, MO (US)

( * ) Notice: Subject to any disclaimer, the term of this patent is extended or adjusted under 35 U.S.C. 154(b) by 18 days.

(21) Appl. No.: 15/872,536

(22) Filed: Jan. 16, 2018

(65) Prior Publication Data

US 2019/0216074 A1    Jul. 18, 2019

(51) Int. Cl.

| | |
|---|---|
| *A01L 15/00* | (2006.01) |
| *A61K 47/44* | (2017.01) |
| *A61K 9/00* | (2006.01) |
| *A61D 11/00* | (2006.01) |
| *A01K 13/00* | (2006.01) |
| *A61K 9/06* | (2006.01) |
| *A61K 47/06* | (2006.01) |
| *A61P 17/00* | (2006.01) |
| *A61K 31/65* | (2006.01) |

(52) U.S. Cl.
CPC .......... *A01L 15/00* (2013.01); *A01K 13/007* (2013.01); *A61D 11/00* (2013.01); *A61K 9/0017* (2013.01); *A61K 9/06* (2013.01); *A61K 47/06* (2013.01); *A61K 47/44* (2013.01); *A61P 17/00* (2018.01); *A61K 31/65* (2013.01)

(58) Field of Classification Search
CPC ......... A01L 15/00; A61K 9/06; A61K 9/0017; A61K 47/44; A61K 31/65; A61K 47/06; A01K 13/007; A61D 11/00; A61P 17/00
See application file for complete search history.

(56) References Cited

U.S. PATENT DOCUMENTS

| | | |
|---|---|---|
| 3,304,227 A | 2/1967 | Loveless |
| 3,491,187 A | 1/1970 | Ely |
| 4,859,694 A | 8/1989 | Pavlich |
| 5,374,432 A | 12/1994 | Fox, Jr. et al. |
| 6,241,992 B1 | 6/2001 | Morck et al. |
| 6,387,383 B1 | 5/2002 | Dow et al. |
| 8,586,102 B2 * | 11/2013 | Rocker ................ A61K 9/0017 424/642 |
| 9,107,418 B2 | 8/2015 | Smithyman et al. |
| 2006/0110415 A1 | 5/2006 | Gupta |
| 2008/0166424 A1 | 7/2008 | Mixon et al. |
| 2008/0286235 A1 * | 11/2008 | Beierle ................ A01N 37/44 424/93.1 |
| 2009/0173288 A1 * | 7/2009 | Pigg ........................ A01L 15/00 119/651 |
| 2010/0234460 A1 | 9/2010 | Foret et al. |
| 2012/0177747 A1 | 7/2012 | Sookram et al. |
| 2013/0122115 A1 * | 5/2013 | Kehoe .................... A61K 33/18 424/667 |

FOREIGN PATENT DOCUMENTS

| | | |
|---|---|---|
| WO | 2009053934 A2 | 4/2009 |
| WO | 2013079604 A1 | 6/2013 |
| WO | 20140134709 A1 | 9/2014 |

OTHER PUBLICATIONS

Aquaphor. Product Sheet [online]. eMedTV, 2012 [retrieved on May 28, 2019]. Retrieved from the Internet:, 2 pages. (Year: 2012).*
Ceresin Wax. Information Sheet [online]. Chemical Book, 2017 [retrieved on Jan. 2, 2020]. Retrieved from the Internet:<URL:https://www.chemicalbook.com/ChemicalProductProperty_EN_CB1303742.htm, 3 pages. (Year: 2017).*

* cited by examiner

*Primary Examiner* — Sue X Liu
*Assistant Examiner* — Andriae M Holt
(74) *Attorney, Agent, or Firm* — Robert D. Atkins; Atkins and Associates, P.C.

(57) ABSTRACT

A treatment compound for hoof disease in an animal has a base material and treatment agent. The base material is wax, resin, paste, polymer, oil, or creme. The treatment agent is zinc, copper, oxytetracycline, or tetracycaline. The treatment compound is applied to a hoof area and has a high viscosity in the range of 100,000 to 2,000,000 centipoises to retain the treatment compound on the hoof in a normal animal environment. The treatment compound can be applied by brush, spray, roller, or dipping. The treatment compound is curable by air or UV light to provide a durable, robust shell. The treatment compound can be applied to an interior surface of a boot which is disposed over the hoof to retain the treatment compound on the hoof in normal animal environments. The boot is color coded to indicate length of time that the boot has been applied.

15 Claims, 11 Drawing Sheets

TREATMENT COMPOUND AND METHOD OF APPLICATION FOR HOOF OR FOOT DISEASE IN ANIMALS

FIELD OF THE INVENTION

The present invention relates in general to treatment of disease in an animal and, more particularly, to a treatment compound and method of application for hoof or foot disease in the animal.

BACKGROUND OF THE INVENTION

Diseases and conditions of the foot of animals, particularly ungulates, present major health problems that can cause significant economic losses. While diseases of the hoof are most prevalent in horses, cattle, goats, and sheep, other hoofed animals are all susceptible to pathogens. Sheep have difficulty walking when inflicted with a hoof condition, which is painful for the animal, inflicts stress, and reduces productivity in routine farm and ranch activities. In dairy cows, milk production is lowered because the animals become lethargic and tend to feed less often. Lameness in horses causes animals to lose weight and reduces body conditioning.

Common diseases or conditions of a foot of an animal, particularly the hooves of animals include hairy heel warts, foot rot, and foot scald, typically caused by bacteria. Foot rot, or infectious pododermatitis, is a hoof infection that is commonly found in cattle, sheep, and goats. The disease is extremely painful and contagious and rots away the foot of the animal, more specifically the area between the two toes of the diseased animal. In cattle, foot rot is caused by two anaerobic bacteria, *Fusobacterium necrophorum* and *Bacteroides melaminogenicus*. Both bacteria are common to the environment that cattle live in and *Fusobacterium* is present in the rumen and fecal matter found in the soil of corrals and other fenced areas that keep the animals to confined spaces. The disease is also caused by the microorganism *Diechelobacter nodosus*, which can be found in contaminated soil. The bacteria may originate internally from the animal and be introduced into the soil by fecal matter, or the bacteria may occur naturally in wet soil. Another cause of foot rot may be continuous moisture in the soil and high temperatures or humidity causing the skin between the hooves to crack, allowing the bacteria to infect the foot. Foot rot is prevalent in almost every region of the United States. Foot rot is also prevalent in sheep and goats and is extremely painful, contagious, and causes significant economic loss due to decreased flock production.

Foot scald, also referred to as benign foot rot or interdigital dermatitis, is an inflammation between the toes caused by *F. necrophorum*. Persistent moisture on the skin between the toes can increase susceptibility to foot scald, which can be a precursor to hoof rot. Like foot rot, foot scald outbreaks occur most often during persistent rainy weather along with high temperatures. As with other infectious diseases of the hoof, foot scald causes stress to the animals and can reduce weight gain, reproductive rates, and production. In addition, like other diseases of the hoof, foot scald incurs additional costs to the producer for treatment and increased labor during an outbreak. Introducing an infected animal into a non-contaminated herd can create herd contamination and therefore all animals must be treated.

Papillomatous digital dermatitis, also referred to as Hairy Heel Warts, Footwarts, and Strawberry Foot Disease, is an inflammation of the skin around the hoof of an animal. It is most commonly found at the back of the foot between the bulbs of the heels, but the disease can spread around the foot and into the cleft between the claws. Digital dermatitis is a very painful condition resulting in lameness, and subsequent reduced food intake and fertility.

Common methods for treatment of an infected hoof include antibiotic treatment, chemical treatment, and antimicrobial and disinfectants, often administered with a foot bath. FIG. 1 shows animal 10 with hoofs 14 immersed in treatment solution 16 of foot bath 20. Aqueous treatment solution 16 includes water and antimicrobial agents and disinfectants used in the treatment of infectious diseases of the hoof, such as copper sulfate and zinc sulfate. Animal 10 stands in foot bath 20 for 15-60 minutes. Animal 10 leaves foot bath 20 and returns to the corral or herd with a residual amount of treatment solution 16 remaining on hoofs 14. Treatment solution 16 needs time to work, often days or weeks, in order to neutralize the bacterial infection. Unfortunately, once animal 10 returns to a normal environment, hoofs 14 are again plodding through the bacteria-laden mud. Residual treatment solution 16 on hoof 14 is quickly diluted, dissipated, or washed away by friction with the wet soil as animal 10 moves about a confined space, leaving minimal or no treatment agent remaining on the hoof for any appreciable period of time. The medication applied with foot bath 20 does not remain in contact with hoof 14 long enough to kill the bacteria and enable healing. Once treatment solution 16 is removed by normal activity, there is no longer a barrier against further exposure to the bacterial-laden soil.

Treatment with solution 16 via foot bath 20 is often repeated multiple times, e.g., three treatments, one every five days. Even with multiple treatments, residual treatment solution 16 still does not remain in contact with hoof 14 long enough to be effective. Thus, a central limitation of the prior art is that residual treatment solution 16 is diluted, dissipated, or washed away soon after animal 10 returns to its normal environment, plodding through the mud. Treatment solution 16 simply wears off too soon. Without sufficient time in contact with hoof 14, treatment solution 16 is limited in its effectiveness to cure or regress the disease.

In addition, because residual treatment solution 16 is being washed away when animal 10 returns to corral or heard, the footbath treatments can leave high concentrations of copper in both the soil and water. In some cases, the spent hoof baths are discharged into a manure pit or a lagoon so the copper ultimately spreads onto production ground with the manure, as well as water supplies. The practice can lead to copper accumulation in the soil and water, which is an environmental issue.

While antibiotics can be used to rapidly reduce the severity of diseases such as digital dermatitis there are distinct disadvantages to using antibiotic therapy. Antibiotics can be given by injection or orally with some effectiveness, but require a withdraw period before milk can be used or animal can be slaughtered. The common and extensive use of antibiotics is likely to lead to the production of antibiotic resistant pathogens, which are not only problematic to the animals, but present a general concern to the public. In addition, treatment of herds with antibiotics is prohibitively expensive. Antibiotic therapy, such as injections of long-acting penicillin or oxytetracycline, is effective, however, injections are costly and time consuming and residues may possibly be present in the milk.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

Figure 1:
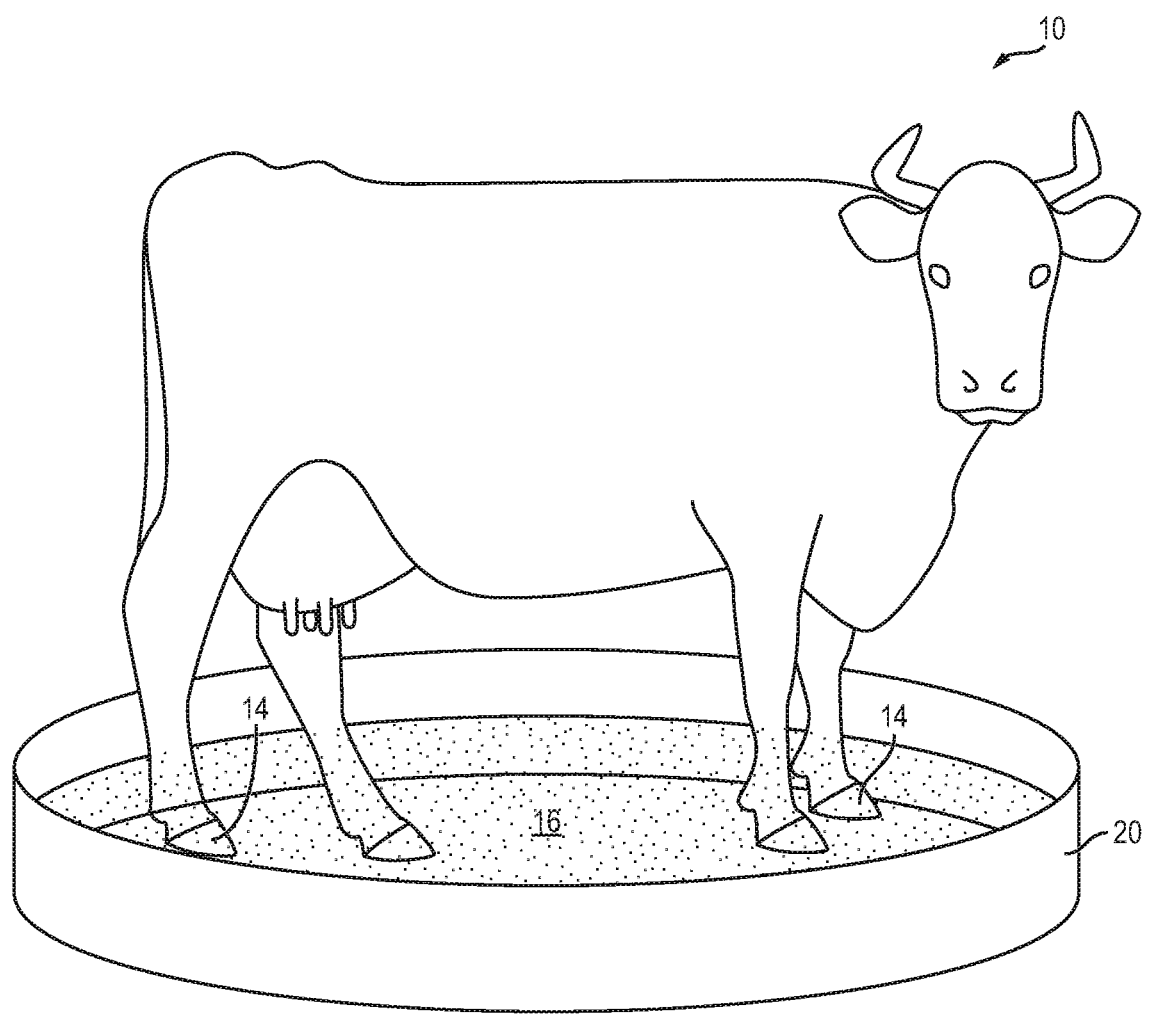
FIG. 1 illustrates an animal receiving hoof disease treatment in a conventional foot bath.
Figure 2:
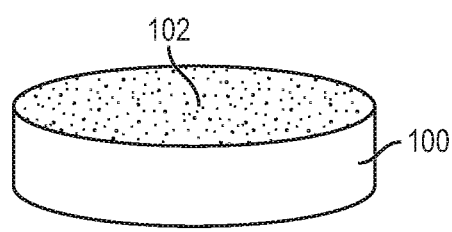
FIG. 2 illustrates a container of wax-based hoof treatment compound.

FIG. 2 illustrates a container 100 with treatment compound 102. In one embodiment, treatment compound 102 includes a wax base material with saturated hydrocarbon molecules derived from petroleum, coal, or oil shale. Treatment compound 102 also includes amounts of one or more treatment agents, such as metal astringents (zinc oxide, zinc sulfate, and copper sulfate), antibiotic agents (oxytetracycline and tetracycaline), and antifungal agents, for the treatment of infectious diseases of the hoof of an animal.

In one embodiment, treatment compound 102 is made by heating wax at a minimum temperature (37° C.) to reach a molten state. Mineral oil and/or petrolatum are added. Next, metal astringents, such as zinc oxide, zinc sulfate, and copper sulfate, are added and mixed in solution. The heat is removed. The mixing operation continues as the solution cools. When the metal astringents begin to suspend in solution, other active ingredients (oxytetracycline, tetracycline, antifungal) and fillers (water and styrene) are added and mixed to an even distribution. Treatment compound 102 cools to room temperature.

Treatment compound 102 contains by volume 15-30% wax, 30-50% mineral oil and/or petrolatum, 20-50% metal astringents, 0-10% other active ingredients, and 0-10% fillers, depending on treatment protocol, disease, environment, and type of animal. Treatment compound 102 is a soft wax or paste at room temperature to simplify application of the treatment agent. In one embodiment, treatment compound 102 has a thick, tacky, strong adhesive properties with a high viscosity in the range of 100,000 to 2,000,000 centipoises, or alternatively in the range of 200,000 to 1,000,000 centipoises, at room temperature to simplify application of the treatment compound and still remain in contact with the hoof for a long duration even in the animal's normal environment. Treatment compound 102 with treatment agent is effective for treatment of foot rot, foot scald, and other bacterial diseases of the hoof.

Figure 3:
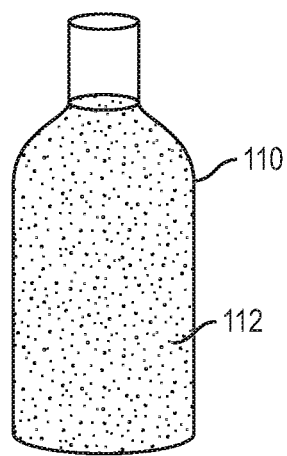
FIG. 3 illustrates a bottle or tube of hoof treatment compound.

FIG. 3 illustrates a bottle or tube 110 with treatment compound 112. Treatment compound 112 includes a liquid, oil, créme, or other base material, with amounts of one or more treatment agents, such as metal astringents (zinc oxide, zinc sulfate, and copper sulfate), antibiotic agents (oxytetracycline and tetracycaline), and antifungal agents, for the treatment of foot rot, foot scald, and other bacterial diseases of the hoof of an animal. Treatment compound 112 has a thick, tacky, strong adhesive properties with a high viscosity in the range of 100,000 to 2,000,000 centipoises, or alternatively in the range of 200,000 to 1,000,000 centipoises, at room temperature to simplify application of the treatment compound and still remain in contact with the hoof for a long duration even in the animal's normal environment.

Figure 4A:
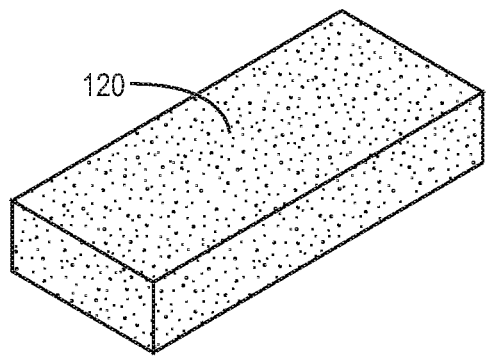
FIGS. 4a-4b illustrate a brick of wax-based hoof treatment compound.
Figure 4B:
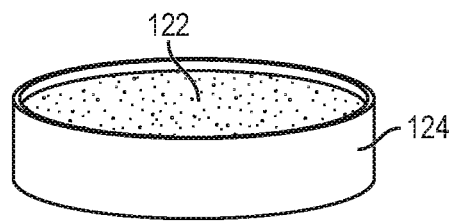

FIG. 4a illustrates a brick 120 as a paraffin wax base material including saturated hydrocarbon molecules derived from petroleum, coal, or oil shale. Brick 120 also includes amounts of one or more treatment agents, such as metal astringents (zinc oxide, zinc sulfate, and copper sulfate), antibiotic agents (oxytetracycline and tetracycaline), and antifungal agents, for the treatment of foot rot, foot scald, and other bacterial diseases of the hoof of the animal. Brick 120 is solid at room temperature and melts at temperatures above 37° C. FIG. 4b shows the paraffin wax base material at an elevated temperature, melted into treatment compound 122 in container 124 to enable application of the treatment agent. In one embodiment, treatment compound 122 has a thick, tacky, strong adhesive properties with a viscosity in the range of 100,000 to 2,000,000 centipoises, or alternatively in the range of 200,000 to 1,000,000 centipoises, to simplify application of the treatment compound and still remain in contact with the hoof for a long duration even in the animal's normal environment.

In other embodiments, the base material can be resin, créme, paste, or polymers. Resin base material can be easily applied and then hardened by ultraviolet (UV) light to form a hard, robust shell to maintain the treatment agent in contact with the hoof for an extended period of time after the animal returns to its normal environment in order to be effective in curing or regress of the disease.

Figure 5A:
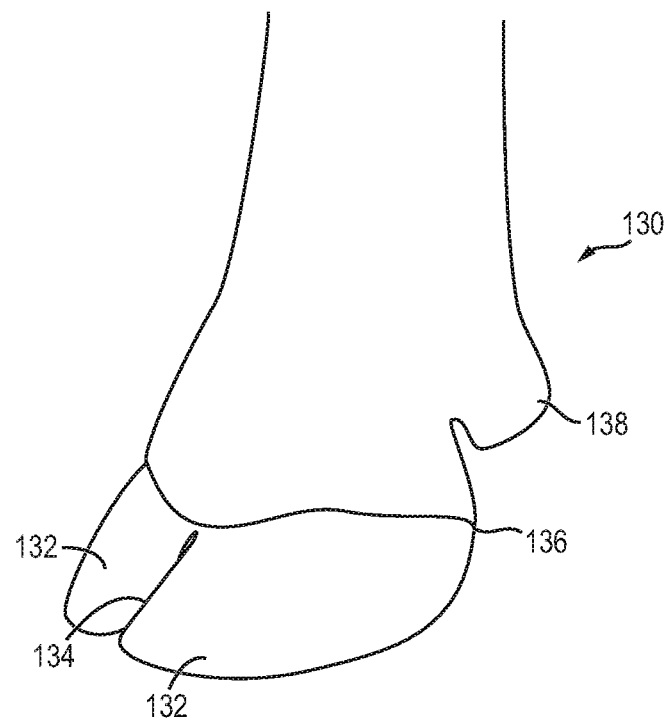
FIGS. 5a-5g illustrate various applications of the hoof treatment compound.

FIG. 5a is a view of hoof 130 of an ungulates animal, such as a horse, cow, goat, sheep, or other hoofed animals. Hoof 130 include claws or toes 132 with cleft 134 between the claws. Bulb 136 is located in an aft part of hoof 130, behind claws 132. Accessory digit 138 is located behind bulb 136. When the animal walks, hoof 130 is lifted off the ground, moves forward, and then contacts the ground leading with claws 132. After making contact with the ground, hoof 130 rolls over so that bulb 136 contacts the ground, followed by accessory digit 138. Claws 132 may spread exposing cleft 134 during each step or contact with the ground. Accordingly, bacteria-laden soil or mud has every opportunity to spread over and lodge into the entire surface area of hoof 130, including into cleft 134, under-side 148 of the hoof, and between bulb 136 and accessory digit 138. Continuing exposure to bacteria, particularly in a wet environment, leads to foot rot and foot scald, which left untreated has significant implications to the animal, as well as to commercial operations of the farm or ranch.

Foot rot is caused by the coexistence of two gram-negative, anaerobic bacteria, *Fusobacterium necrophorum* and *Dichelobacter nodosus* (also referred to as *Bacteroides nodosus*). Several different strains of *D. nodosus* affect both sheep and goats, and can also be carried by cattle, deer, and horses. The bacteria *Fusobacterium necrophorum* causes a common disease known as foot scald. *F. necrophorum* is a natural inhabitant of the large intestine of small ruminants and is found normally in the soil and manure of pastures or feedlots. Infection is exacerbated by wet conditions where mud and manure have been allowed to accumulate. The mud and manure causes interdigital irritation, and *F. necrophorum* readily infects the soft, irritated area. *Dichelobacter nodosus*, the second bacteria, is only capable of living in the soil for 10 to 14 days, yet can survive in the hoof for extended time periods given the right anaerobic environment. The bacteria requires irritation of the interdigital area, possibly due to moisture or trauma, in order to gain entry for infection. Hard frozen ground such as that in dry lots can cause irritation to the soft tissue, and create ideal conditions for foot rot when the ground warms to mud. Foot rot is most prevalent and highly contagious in wet, moist areas. When pastures have been consistently wet with no dry spells there is a higher incidence of outbreaks. The ideal soil reservoir is high in moisture at temperatures between 10° C. to 21° C.

Foot scald and foot rot result in lameness, reduced weight gain, decreased milk and wool production, and decreased reproductive capabilities as severely infected animals are reluctant to move in order to feed. Affected animals often carry the affected leg or lie down for extended periods, rubbing off the wool/hair on their flanks, brisket, and knees. These conditions result in production losses, treatment and prevention costs, premature culling, and reduced sale value of infected animals.

Foot rot, foot scald, and other bacterial diseases of hoof 130 are treatable with treatment compound 102, 112, or 122 (collectively or alternatively referenced as treatment compound 144). Treatment compound 144 contains a base material, such as wax, oil, créme, paste, paraffin, resin, polymer, or other suitable base material, and one or more treatment agents, such as metal astringents (zinc oxide, zinc sulfate, and copper sulfate), antibiotic agents (oxytetracycline and tetracycaline), and antifungal agents. In particular, zinc and copper tend to dry the tissue and hoof area, making it less hospitable for bacteria to grow. Oxytetracycline and tetracycaline retard the ability of bacteria to produce essential proteins necessary for growth, which tends to stop the spread of the infection. Other antibiotics include penicillin, cephalosporins, macrolides, quinolones, vancomycin, sulfonamide/trimethoprim, clindamycin, chloramphenicol, linezolid, synercid, aminoglycosides, monobactams, carbapenems, metronidazole, and ampicillion. Treatment compound 144 may also contain amounts of clotrimazole, econazole nitrate USP, miconazole terbinafine, fluconazole, ketoconazole, amphotericin, and other antifungal agents, for the treatment of infectious diseases of the hoof of the animal. The remaining bacteria are killed by the immune system or eventually die.

One aspect of the present invention is to apply treatment compound 144 in a manner that the treatment agents remain in contact with hoof 130 for a sufficient period of time to be effective against the hoof disease. The treatment agents cure or regress the disease, the base material forms a hard, durable shell to keep the treatment agents in contact with hoof 130 for the requisite time period for the treatment agents to be effective, even when the animal returns to its normal environment.

Figure 5B:
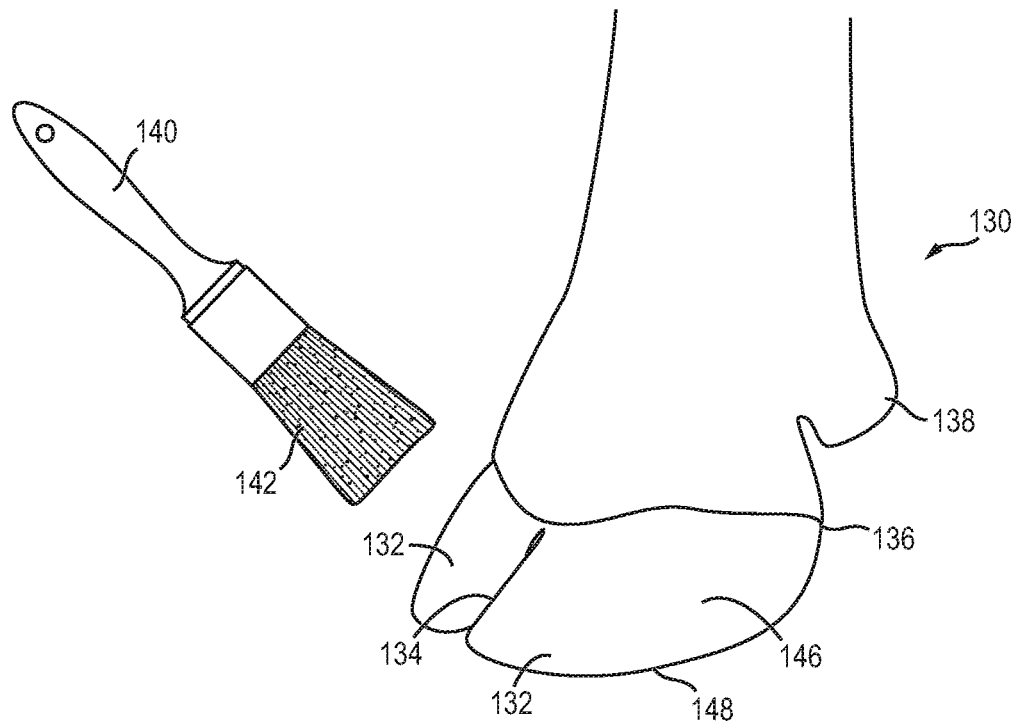
Figure 6A:
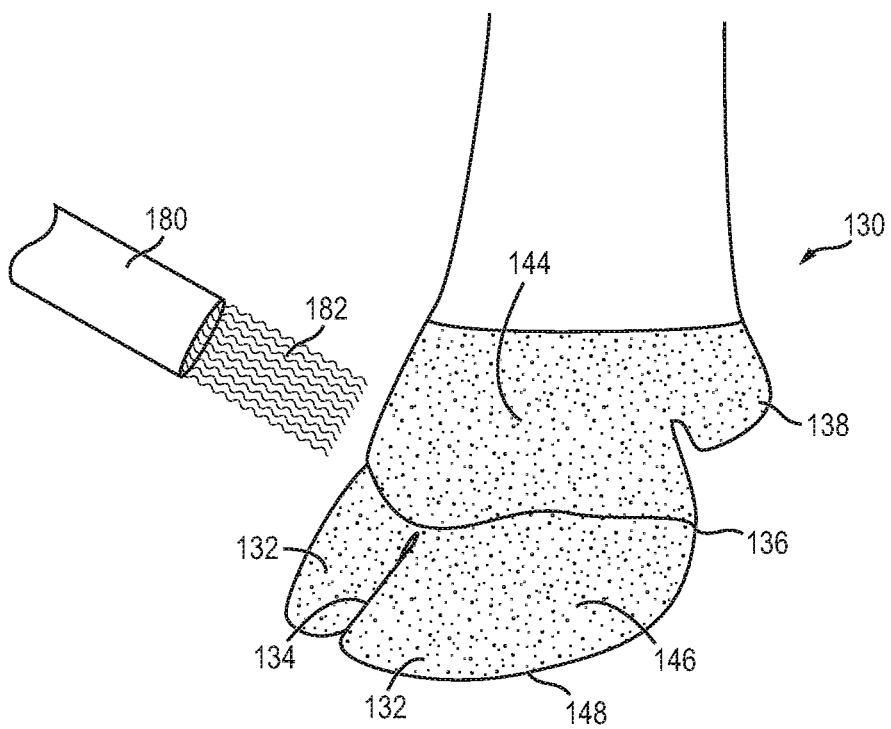
FIGS. 6a-6c illustrate curing of the treatment compound on a hoof.
Figure 6B:
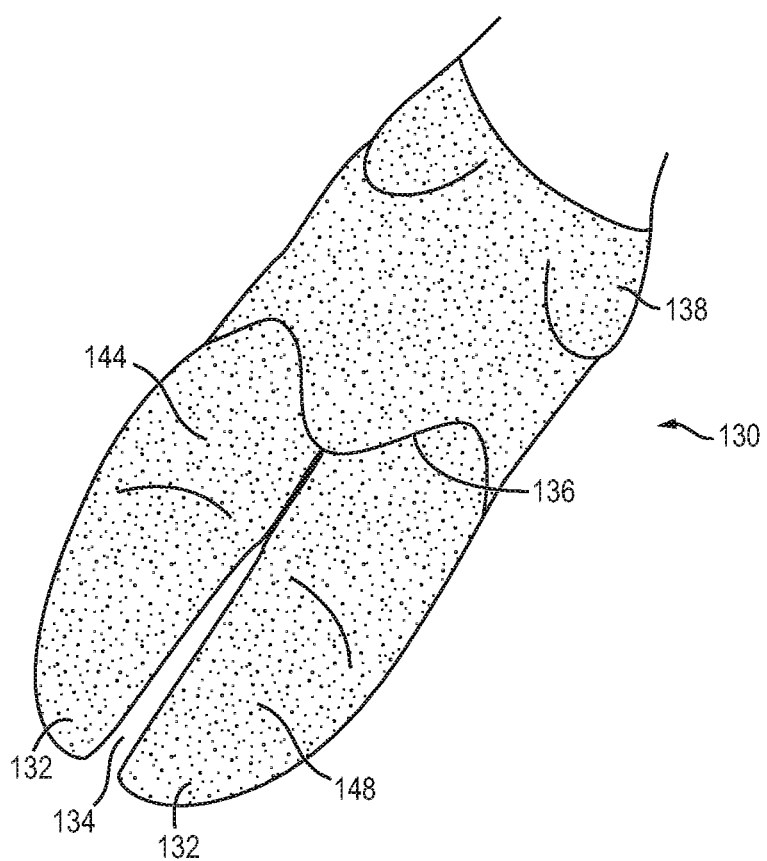

In FIG. 5b, brush 140 is dipped or immersed into a container of treatment compound 144, see FIG. 2, 3, or 4b. Bristles 142 of brush 140 pick up an amount of treatment compound 144 for application to hoof 130. In particular, treatment compound 144 is spread as a thick layer using brush 140, e.g., 0.5-5.0 millimeters (mm), over wall 146 of claws 132, as well as into cleft 134 between the claws. Treatment compound 144 is also applied to underside surface 148 of hoof 130, including bulb 136 and accessory digit 138. Treatment compound 144 covers all surfaces of hoof 130 which are susceptible to or inflicted by foot rot, foot scald, and other bacterial diseases of the hoof. Alternatively, treatment compound 144 is applied to hoof 130 by hand, preferably wearing a glove. FIG. 6a shows treatment compound 144 applied to wall 146 of claws 132 and into cleft 134. FIG. 6b shows treatment compound 144 applied to underside surface 148 of hoof 130, including bulb 136 and accessory digit 138.

Figure 5C:
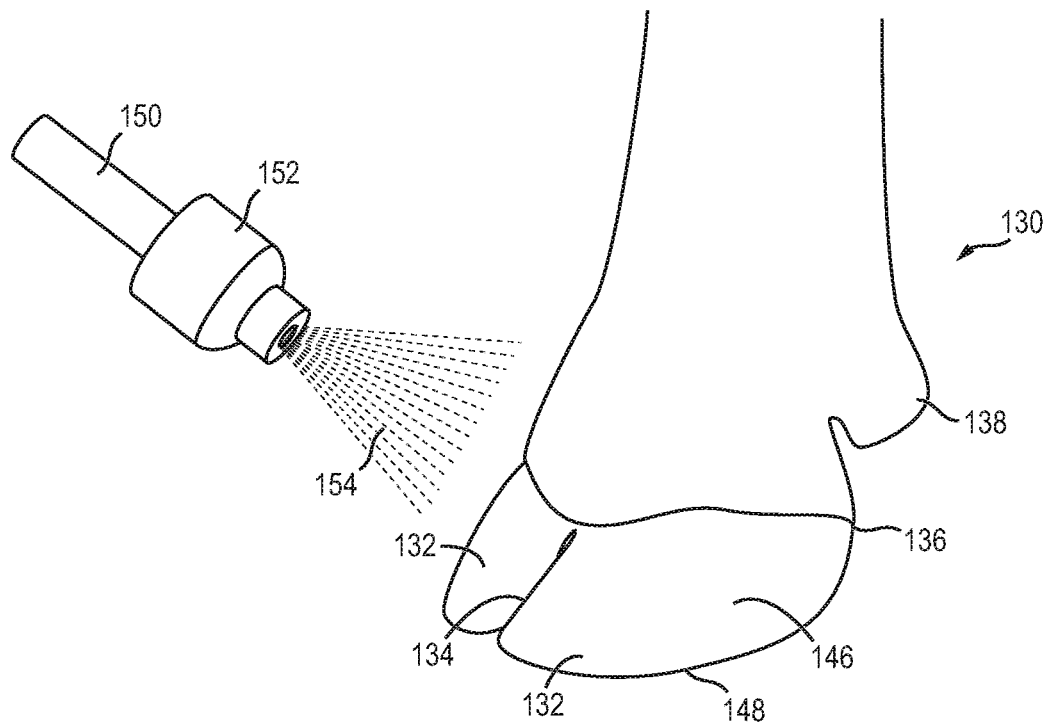

In FIG. 5c, sprayer 150 is provided with a supply of treatment compound 144, see FIG. 2, 3, or 4b. Spray head 152 applies a thick layer (0.5-5.0 mm) of treatment compound 144 over wall 146 of claws 132, as well as into cleft 134 between the claws, see FIG. 6a. Treatment compound 144 is also sprayed over underside surface 148 of hoof 130, including bulb 136 and accessory digit 138, see FIG. 6b. Treatment compound 144 covers all surfaces of hoof 130 which are susceptible to or inflicted by foot rot, foot scald, and other bacterial diseases of the hoof.

Figure 5D:
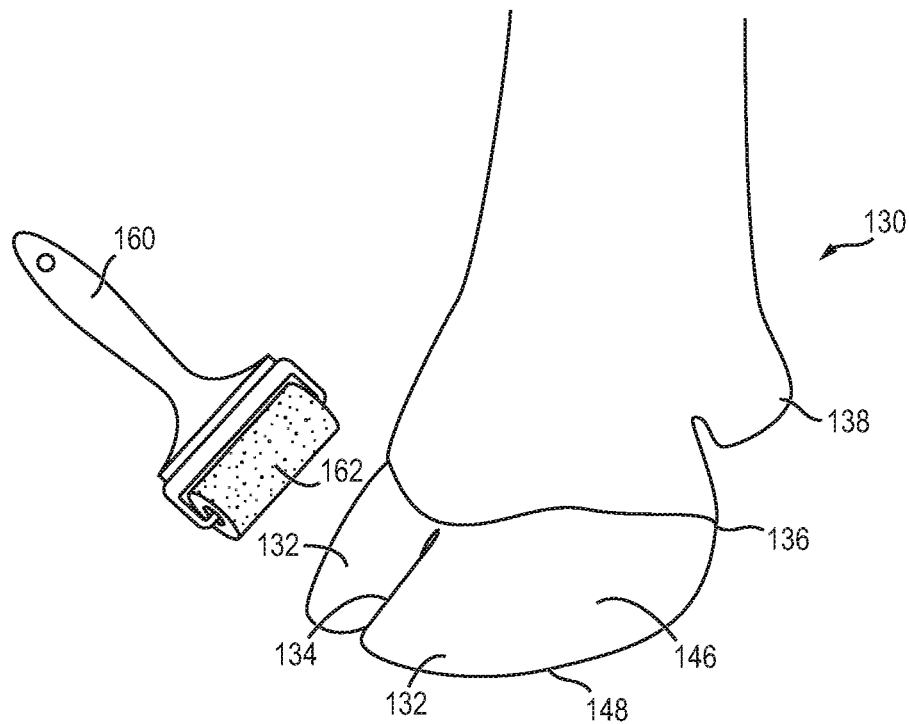

In FIG. 5d, roller 160 picks up an amount of treatment compound 144, see FIG. 2, 3, or 4b. Roller surface 162 applies a thick layer (0.5-5.0 mm) of treatment compound 144 over wall 146 of claws 132, as well as into cleft 134 between the claws, see FIG. 6a. Treatment compound 144 is also applied to underside surface 148 of hoof 130, including bulb 136 and accessory digit 138, see FIG. 6b. Treatment compound 144 covers all surfaces of hoof 130 which are susceptible to or inflicted by foot rot, foot scald, and other bacterial diseases of the hoof.

Figure 5E:
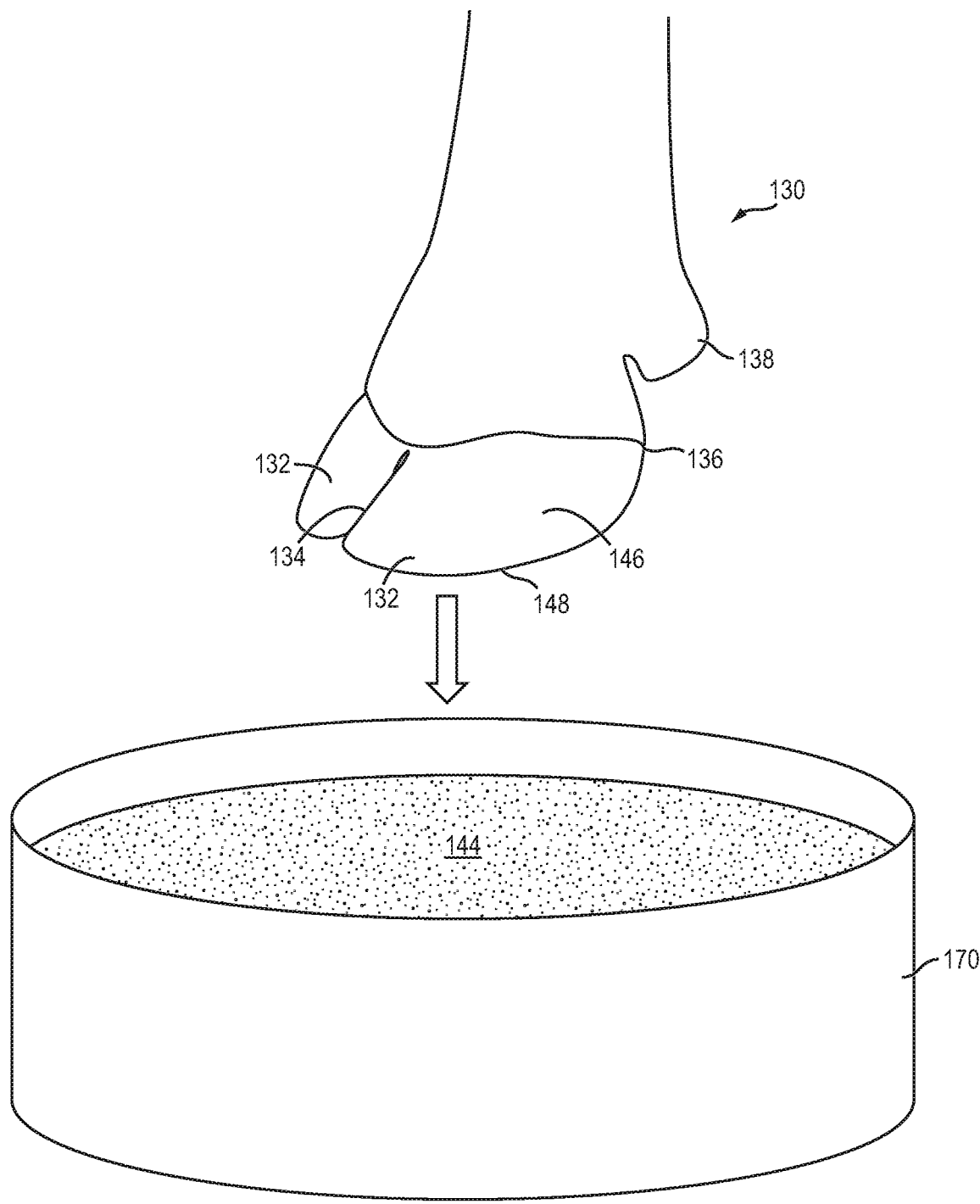
Figure 5F:
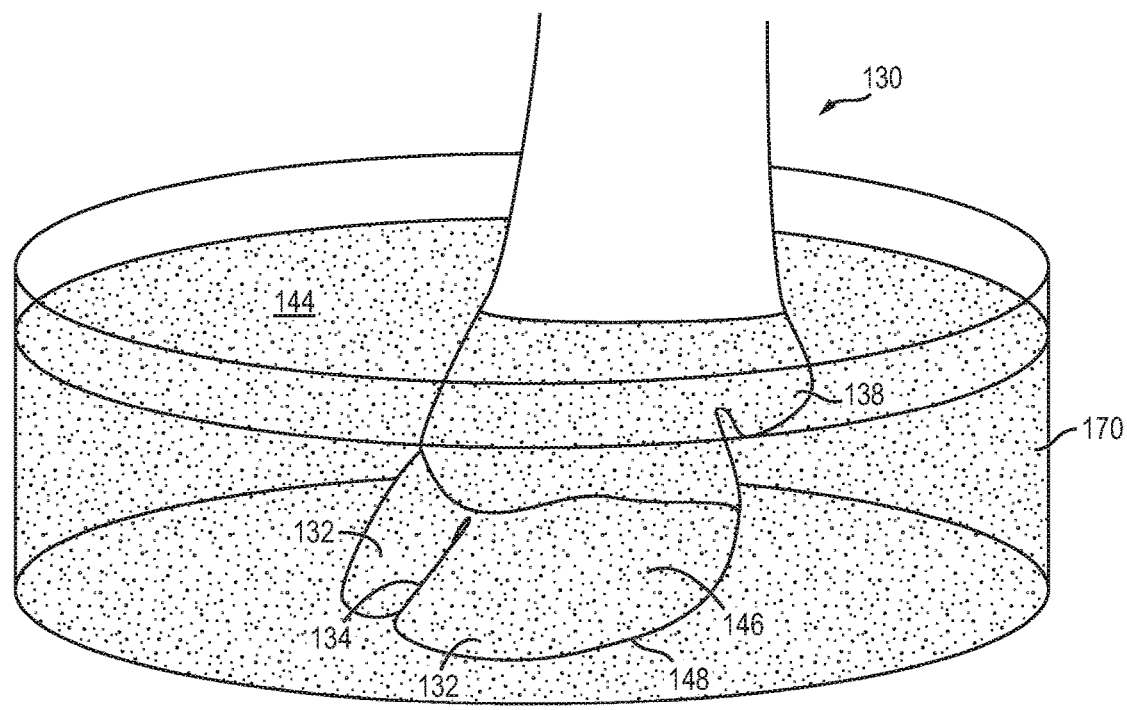

In FIG. 5e, hoof 130 is dipped directly into container 170 filled with treatment compound 144. FIG. 5f shows hoof 130 immersed in container 170. Hoof 130 is then removed from container 170 leaving a thick layer (0.5-5.0 mm) of treatment compound 144 over wall 146 of claws 132, as well as into cleft 134 between the claws, see FIG. 6a. Treatment compound 144 also covers underside surface 148 of hoof 130, including bulb 136 and accessory digit 138, see FIG. 6b. Treatment compound 144 covers all surfaces of hoof 130 which are susceptible to or inflicted by foot rot, foot scald, and other bacterial diseases of the hoof. After removing hoof 130 from container 170, a brush, spreader, or detail tool can be used to further spread or even out treatment compound 144 to ensure all surfaces of the hoof are thoroughly covered with the treatment compound.

Figure 5G:
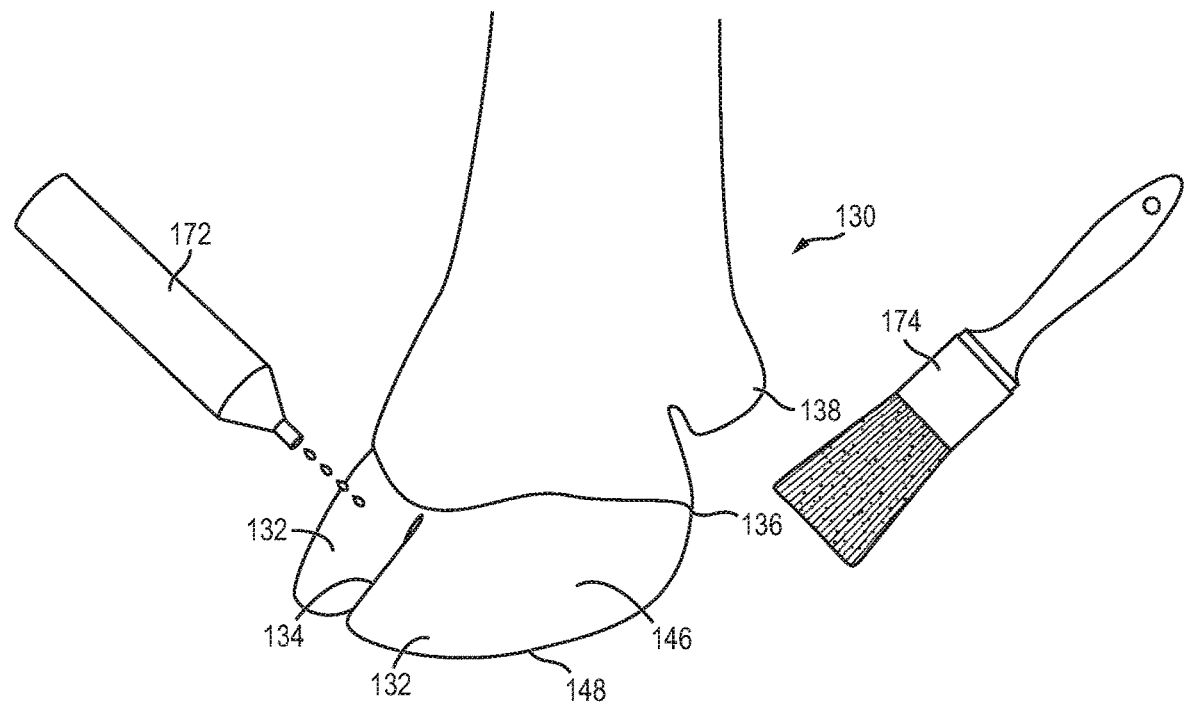

In FIG. 5g, treatment compound 144 is applied to hoof 130 using tube applicator 172 with a pump or squeeze operation. Treatment compound 144 is then evenly spread as a thick layer (0.5-5.0 mm) using brush 174, over wall 146 of claws 132, as well as into cleft 134 between the claws, see FIG. 6a. Treatment compound 144 is also applied to underside surface 148 of hoof 130, including bulb 136 and accessory digit 138, see FIG. 6b. Treatment compound 144 covers all surfaces of hoof 130 which are susceptible to or inflicted by foot rot, foot scald, and other bacterial diseases of the hoof.

The base material (wax, paraffin, oil, resin, paste, polymer, etc.) serves to maintain the treatment agent in contact with hoof 130 for a longer period of time after the animal returns to its normal environment. Treatment compound 144 is a thick, tacky material with strong adhesive properties, even in a wet environment, and thus robust to the ground friction and other forces that would otherwise act to dilute, dissipate, or remove the treatment compound as the animal moves about in its normal moist soil or mud environment. In addition, treatment compound 144 acts as a barrier to reduce further exposure to the bacterial-laden soil.

Figure 6C:
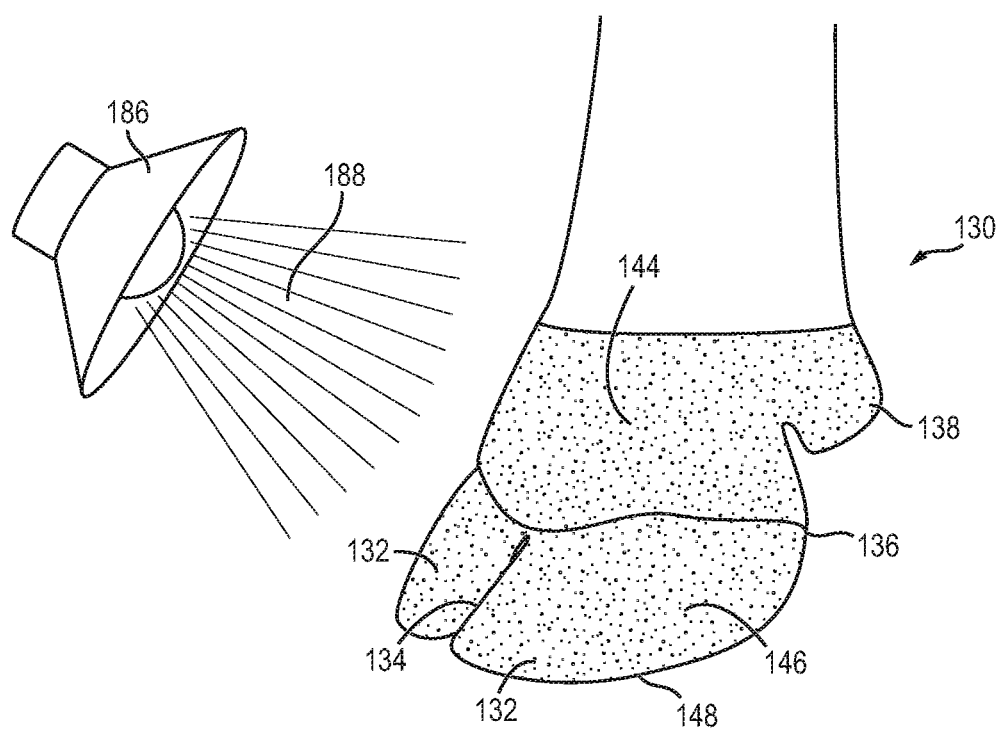

In one embodiment, after application of treatment compound 144 to hoof 130 using one or more of the techniques described in FIGS. 5a-5g, the treatment compound is cured. FIGS. 6a-6b show air blower 180 forcing cool or room temperature air across all surfaces of hoof 130 to dry out and solidify treatment compound 144. Alternatively, the treatment compound is cured by ultra-violet (UV) light 186, as shown in FIG. 6c. UV rays 188 harden treatment compound 144, for example when using base materials containing UV responsive resin materials.

The curing process forms a durable shell coverage of treatment compound 144, by action of curing the base material, to form a moisture tight seal which is robust to the ground friction and other forces that would otherwise act to dilute, dissipate, or remove the treatment compound once the animal returns to its normal environment. The treatment agents remain in contact with hoof 130 for a sufficient period of time to be effective against the hoof disease. The treatment agents cure or regress the disease. The base material (wax, paraffin, oil, resin, paste, polymer, etc.) serves to maintain the treatment agent in contact with hoof 130 for a longer period of time after the animal returns to move about in its normal moist soil or mud environment. In addition, treatment compound 144 acts as a robust barrier to reduce further exposure to the bacterial-laden soil. Treatment compound 144 can be reapplied as indicated.

Figure 7A:
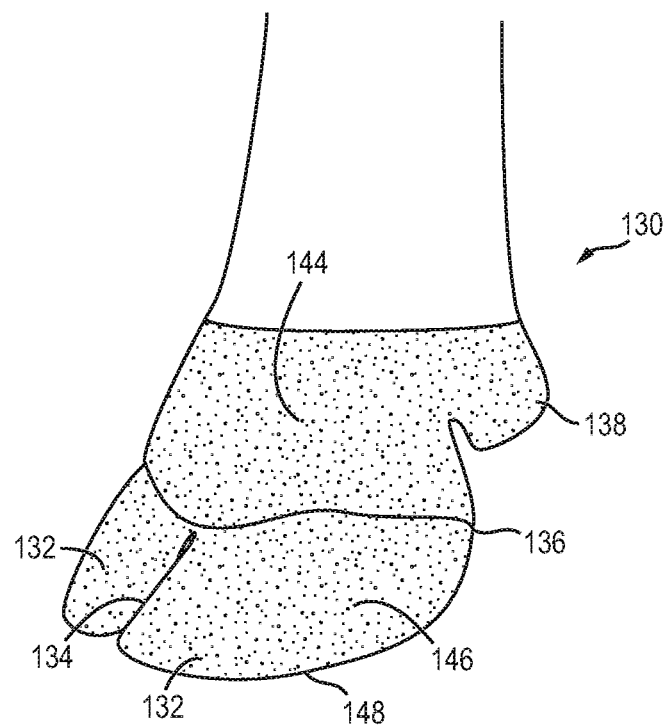
FIGS. 7a-7b illustrate an alternate treatment with the treatment compound applied over the hoof and a protective layer disposed around the hoof over the treatment compound.
Figure 7B:
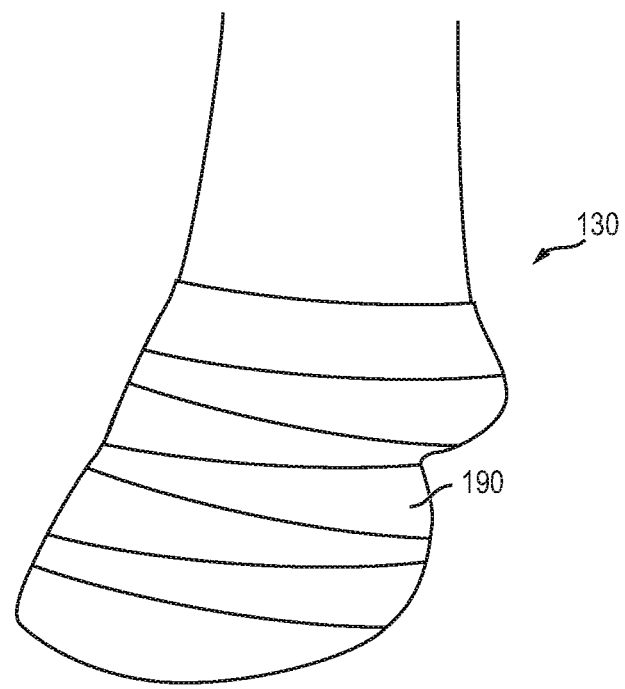

FIGS. 7a-7b illustrate another embodiment where treatment compound 144, including base material and treatment agent, is applied to hoof 130 and then wrapped with a protective layer 190. In FIG. 7a, treatment compound 144 is applied to hoof 130, as described in FIGS. 5a-5g. In FIG. 7b, hoof 130 is wrapped with protective layer 190, such as a durable, watertight fabric, tape, gauze, wrap, or other covering. Protective layer 190 can be made with nylon, latex, vinyl, or Gore Tex. Alternatively, a natural or synthetic fabric is laminated or coated with a waterproof material, such as rubber, polymer, polypropylene, polyvinyl chloride, polyurethane, silicone elastomer, fluoropolymers, or wax. The close fit of protective layer 190 causes treatment compound 144 to maintain contact with hoof 130, including wall 146 of claws 132, cleft 134 underside surface 148, bulb 136, and accessory digit 138. Treatment compound 144 under protective layer 190 covers all surfaces of hoof 130 which are susceptible to or inflicted by foot rot, foot scald, and other bacterial diseases of the hoof.

Protective layer 190 serves to maintain treatment compound 144, and corresponding treatment agent, in contact with hoof 130 for a longer period of time after the animal returns to its normal environment. Protective layer 190 is robust to the ground friction and other forces that would otherwise act to dilute, dissipate, or remove treatment compound 144 as the animal moves about in its normal moist soil or mud environment. In addition, protective layer 190 acts as a barrier to reduce further exposure to the bacterial-laden soil.

Figure 8A:
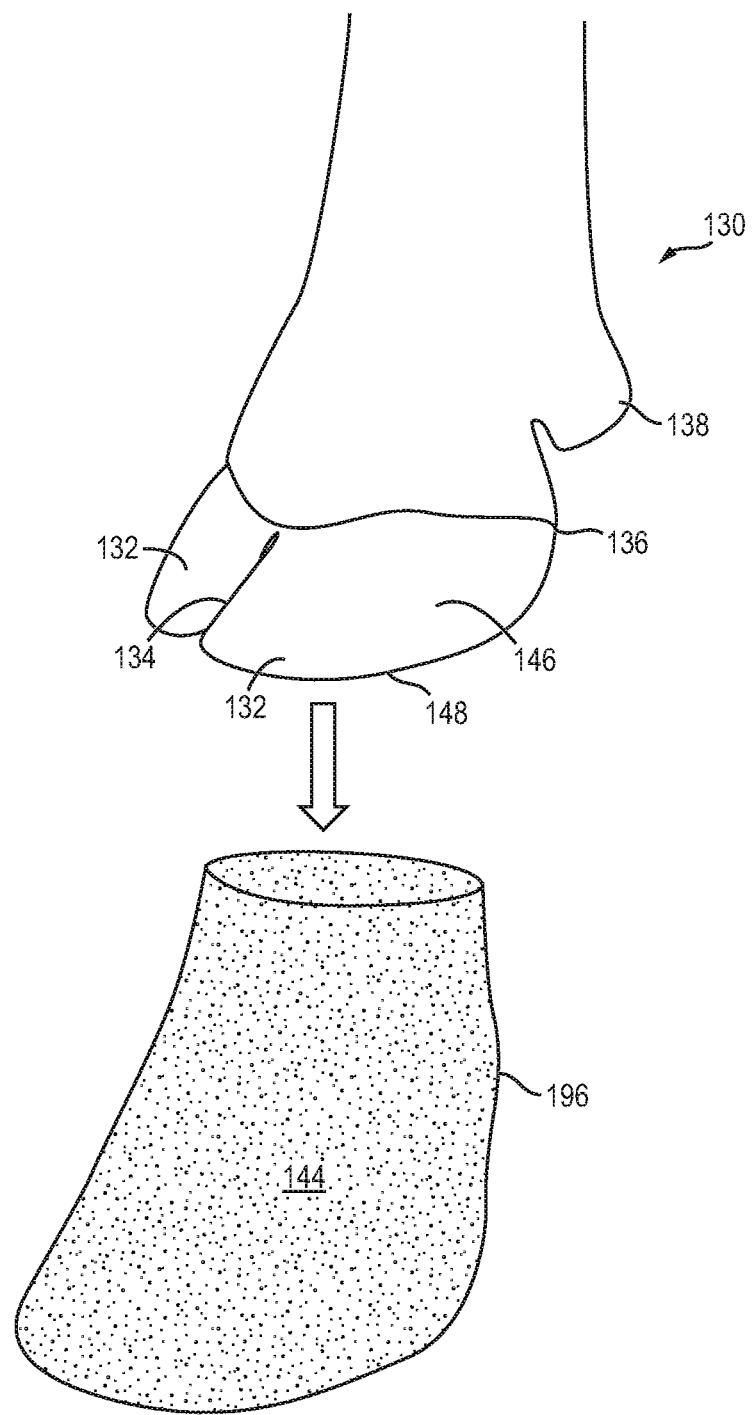
FIGS. 8a-8b illustrate an alternate treatment with a boot disposed over the hoof and containing the treatment compound applied to an interior surface of the boot.
Figure 8B:
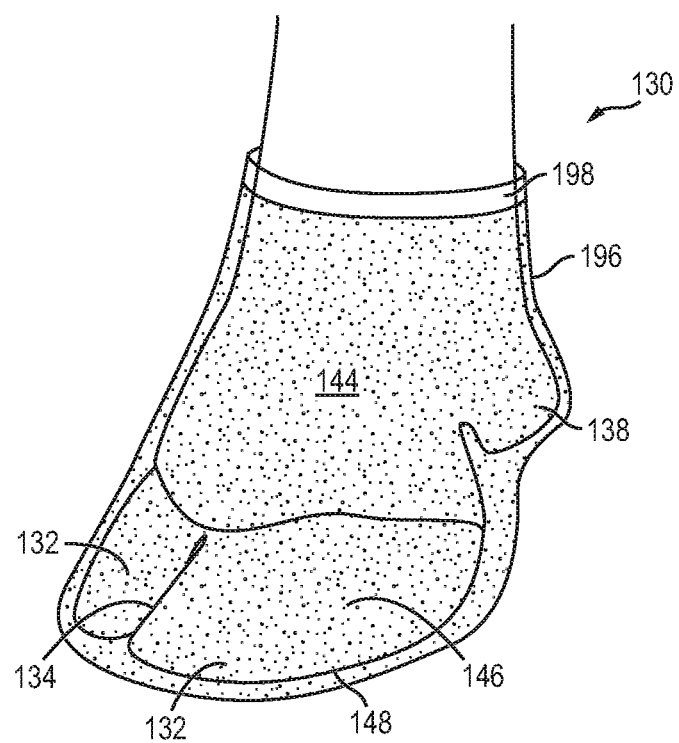

FIGS. 8a-8b illustrate another embodiment where treatment compound 144, including base material and treatment agent, is applied to an interior surface of boot or sleeve 196. In FIG. 8a, boot 196 containing treatment compound 144 is positioned to be disposed over hoof 130. Boot 196 is a durable, watertight fabric, such as nylon, latex, vinyl, or Gore Tex. Alternatively, a natural or synthetic fabric is laminated or coated with a waterproof material, such as rubber, polymer, polyvinyl chloride, polyurethane, silicone elastomer, fluoropolymers, or wax. Treatment compound 144 can be applied to hoof 130 prior to placing boot 196 over the hoof, as described in FIGS. 5a-5g.

FIG. 8b shows boot 196 covering hoof 130. Boot 196 fits snugly against hoof 130 and is held in place with a draw string, tape, plastic wrap, adhesive, Velcro, or other securing mechanism. The close fit of boot 196 causes treatment compound 144 covering the interior surface of the boot to maintain contact with hoof 130, including wall 146 of claws 132, cleft 134 underside surface 148, bulb 136, and accessory digit 138. Treatment compound 144 in boot 196 covers all surfaces of hoof 130 which are susceptible to or inflicted by foot rot, foot scald, and other bacterial diseases of the hoof.

Boot 196 serves to maintain treatment compound 144, and corresponding treatment agent, in contact with hoof 130 for a longer period of time after the animal returns to its normal environment. Boot 196 is robust to the ground friction and other forces that would otherwise act to dilute, dissipate, or remove treatment compound 144 as the animal moves about in its normal moist soil or mud environment. In addition, boot 196 acts as a barrier to reduce further exposure to the bacterial-laden soil.

Protective layer 190 or boot 196 can be coded or marked with colored ring, band, label, or marker 198 to indicate the day that the boot and treatment compound was applied. For example, a red color ring 198 on boot 196 for certain animals can be recorded as being applied on March 1, and a green color ring 198 on other animals can be recorded as being applied on March 10. Alternatively, the entire surface of boot 196 can be color coded to indicate the date applied. The rancher or farmer can then determine by visual inspection the period of time that boot 196 has been applied to each animal and remove as directed. Boot 196 remains in place on hoof 130 with treatment compound 144 working on the infected hoof for an optimal time period, as determined by a veterinarian.

While one or more embodiments of the present invention have been illustrated in detail, the skilled artisan will appreciate that modifications and adaptations to those embodiments may be made without departing from the scope of the present invention as set forth in the following claims.

What is claimed:

1. A method of treating hoof disease in an animal, comprising:
    providing a treatment compound including each by volume,
        (a) a wax material of 15-30%,
        (b) a mineral oil or petrolatum of 30-50%,
        (c) a metal astringent of 20-50%,
        (d) a filler of up to 10%, and
        (e) an active ingredient up to 10%; and
    applying the treatment compound to a hoof area, wherein the treatment compound includes a viscosity in the range of 100,000 to 2,000,000 centipoises to retain the treatment compound on the hoof area in a normal animal environment for a sufficient time to be effective in treating hoof disease in the animal.

2. The method of claim 1, further including curing the treatment compound.

3. The method of claim 1, wherein the active ingredient includes antibiotic agent or antifungal agent.

4. The method of claim 1, further including applying the treatment compound by brush, tube, spray, roller, dipping, or by hand.

5. The method of claim 1, wherein the treatment compound covers an entire surface area of the hoof susceptible to or inflicted by the hoof disease.

6. The method of claim 1, wherein the wax material is a solid at room temperature.

7. The method of claim 1, further including disposing a boot or protective layer over the treatment compound.

8. The method of claim 1, wherein the metal astringent is selected from the group consisting of zinc oxide, zinc sulfate, and copper sulfate.

9. The method of claim 7, further including providing a color coded marker on the boot or protective layer.

10. A treatment compound for hoof disease in an animal, comprising:
   a wax material of 15-30%;
   a mineral oil or petrolatum of 30-50%;
   a filler of up to 10%; and
   a treatment agent including a metal astringent of 20-50%, and an antibiotic or antifungal agent up to 10%, wherein the treatment compound includes a viscosity in the range of 100,000 to 2,000,000 centipoises to retain the treatment agent remain on a hoof area of the animal in a normal animal environment for a sufficient time to treat hoof disease in the animal.

11. The treatment compound of claim 10, wherein the wax material is a curable material.

12. The treatment compound of claim 10, wherein the wax material is a solid at room temperature.

13. The treatment compound of claim 10, further including a boot or protective layer disposed over the treatment compound.

14. The treatment compound of claim 10, wherein the metal astringent is selected from the group consisting of zinc oxide, zinc sulfate, and copper sulfate.

15. The treatment compound of claim 13, further including a color coded marker on the boot or protective layer.

\* \* \* \* \*

UNITED STATES PATENT AND TRADEMARK OFFICE
CERTIFICATE OF CORRECTION

PATENT NO. : 10,779,525 B2
APPLICATION NO. : 15/872536
DATED : September 22, 2020
INVENTOR(S) : John P. Sanchez, Diane Sanchez and Michael Sanchez It is certified that error appears in the above-identified patent and that said Letters Patent is hereby corrected as shown below:

In the Claims

Column 9, Claim 10, Line 17, delete the word "remain".

Signed and Sealed this
Twentieth Day of October, 2020

Andrei Iancu
*Director of the United States Patent and Trademark Office*